United States Patent [19]

Bayard et al.

[11] 4,338,933

[45] Jul. 13, 1982

[54] COMBINATION QUICK DISCONNECT COUPLING AND LIQUID CUTOFF VALVE

[75] Inventors: Michael A. Bayard, Chicago; James A. Turnbull, Grayslake, both of Ill.

[73] Assignee: Abbott Laboratories, North Chicago, Ill.

[21] Appl. No.: 219,017

[22] Filed: Dec. 22, 1980

[51] Int. Cl.³ .............................................. A61M 5/14
[52] U.S. Cl. ........................... 128/214 R; 251/149.1; 128/274
[58] Field of Search ...................... 128/214, 214.2, 272, 128/272.3, 272.2, 274, 218 M; 137/67, 318; 251/342, 343, 353, 149, 149.2, 149.9, 149.5

[56] References Cited

U.S. PATENT DOCUMENTS

| | | | |
|---|---|---|---|
| 745,815 | 12/1903 | Gibson | 285/3 |
| 808,446 | 12/1905 | Gill et al. | 285/3 |
| 968,711 | 8/1910 | Stevenson | 128/766 |
| 1,580,312 | 4/1926 | Long | 128/766 |
| 2,275,477 | 3/1942 | Sundholm | 251/149.8 |
| 2,502,206 | 3/1950 | Creek | 251/149.1 |
| 3,588,149 | 6/1971 | Demler et al. | 285/110 |
| 3,626,980 | 12/1971 | Svensson | 251/149 X |
| 3,707,972 | 1/1973 | Vilvari et al. | 128/214 X |
| 3,876,234 | 4/1975 | Harms | 285/38 |
| 3,986,508 | 10/1976 | Barrington | 128/214.2 |
| 4,019,512 | 4/1977 | Tenczar | 128/214 R |
| 4,022,205 | 5/1977 | Tenczar | 128/214 R |
| 4,030,494 | 6/1977 | Tenczar | 128/214 R |
| 4,046,145 | 9/1977 | Choksi et al. | 128/215 |
| 4,055,179 | 10/1977 | Manschot et al. | 128/275 |
| 4,056,116 | 11/1977 | Carter et al. | 137/68 R |
| 4,076,285 | 2/1978 | Martinez | 285/332 |
| 4,080,965 | 3/1978 | Phillips | 128/214 D |
| 4,133,312 | 1/1979 | Burd | 128/214 |
| 4,161,949 | 7/1979 | Thanawalla | 128/247 |
| 4,186,752 | 2/1980 | Guerra | 128/766 |
| 4,201,406 | 5/1980 | Dennehey et al. | 285/3 |

FOREIGN PATENT DOCUMENTS

2809303  3/1978  Fed. Rep. of Germany .

Primary Examiner—Stephen C. Pellegrino
Attorney, Agent, or Firm—Robert L. Niblack; Robert S. Beiser

[57] ABSTRACT

A combination quick disconnect coupling and liquid cutoff valve comprises a first tubular member, and a second tubular member having a cylindrical sheath slidably disposed about and extending therefrom, sized for telescopic insertion into the first tubular member. The first and second tubular members may be coupled together and retained in that position as required. Two fluid passageways extend through the second tubular member. A third tubular member is concentrically positioned within the second tubular member and has a resilient, releasable, penetrable diaphragm at one end. A piercing pin is disposed within the movable cylindrical sheath so that when the piercing pin is exterior to the diaphragm, a first liquid passes through the connector, but when the piercing pin is inserted through the penetrable diaphragm, a second liquid passes through the connector and the flow of the first liquid is shut off.

23 Claims, 14 Drawing Figures

COMBINATION QUICK DISCONNECT COUPLING AND LIQUID CUTOFF VALVE

BACKGROUND OF THE INVENTION

The present invention relates generally to the field of connector mechanisms for fixedly joining together the ends of two pieces of flexible tubing in a manner which is disengageable, but which resists accidental disconnection. Connectors of this general type are capable of a wide variety of uses, but are particularly useful in forming fluid connections between pieces of flexible tubing utilized in a wide variety of medical and surgical devices in hospitals and similar environs. The connector or coupling of the present invention was developed specifically for use in continuous ambulatory peritoneal dialysis.

Prior to the present invention, connectors of this general type have been used for many years to effectuate rapid and effective junctions between pieces of tubing. A requirement of such connectors is that a fluid tight seal be obtained. Another requirement is that the connection, once made, should be strongly resistant to inadvertent disengagement, but should be readily disengageable when desired by simple and rapid manual manipulation.

Exemplary of prior art coupling devices or valves used in medical applications are the following U.S. patent Nos.:

4,055,179—Valve for Urinary Drainage Container or Similar Article—James Gordon Manschot, et al.—granted 10/25/77;
3,588,149—Vacuum or Pressure Coupling Devices—Henry William Demier, Sr., et al.—granted 6/28/71;
4,046,145—Syringe Connector—Pradip Vinobchandra Choksi, et al.—granted 9/6/77;
3,876,234—Twist-Lock Connector—Jack L. Harms—granted 4/8/75;
4,133,312—Connector for Attachment of Blood Tubing to External Arteriovenous Shunts—Samuel Burd—granted 1/9/79;
Method and Apparatus for Continuous, Ambulatory Peritoneal—Robert P. Popovich—Abandoned;
4,161,949—Aseptic Connector—Chandrakant B. Thanawalla—granted 7/24/79;
4,019,512—Adhesively Activated Sterile Connector—Francis J. Tanczar—granted 4/26/77;
4,056,116—Valve for Interconnecting Sterile Containers and the like—Garry L. Carter, et al.—granted 11/1/77;
4,080,965—In-Line Cannula Valve Assembly—Thomas E. Phillips—granted 3/28/78;
4,022,205—Fluid Connectors—Francis J. Tenczar—granted 5/10/77;
4,076,285—Laminar Flow Connector for Conduits—Felix Jesus martinez—granted 2/28/78;
4,030,494—Fluid Connectors;13 Francis Tenczar—granted 6/21/77;
4,201,406—Spike Connector for Solution Bag—T. Michael Dennehey—granted 5/6/80;
745,815—Hose-Coupling—William W. Gibson—granted 12/1/03;
808,446—Coupling—L. D. Gill, et al.—granted 12/26/05;
4,186,752—Device for Taking Blood and For Injecting Medication—Luis A. Guerra—granted 2/5/80;
1,580,312—Combined Plug Valve and Hose Connection—J. F. Long—granted 4/13/26;
968,711—Hydrant—J. W. Stevenson—granted 8/30/10.

In the field of peritoneal dialysis, a relatively high rate of peritonitis has been found. It is suspected that this is due to the passage of microorganisms through the connecting mechanism utilized, and hence into the peritoneal cavity of the patient. In order to prevent such microbial contamination, it is an advantage of the present invention to provide a combination quick disconnect coupling and fluid cutoff valve, which prevents access to the peritoneal cavity except when both halves of the coupling are engaged. It is an additional advantage of the present invention to provide such a coupling mechanism which is relatively easy to manipulate and inexpensive to manufacture.

An additional requirement in continuous ambulatory peritoneal dialysis is the drainage of dialysate from the peritoneal cavity and the subsequent introduction of fresh dialysate. It is an additional advantage of the present invention to provide a valving mechanism which subsequently performs these functions within the connector mechanism, thereby minimizing bacterial contamination.

SUMMARY OF THE INVENTION

The foregoing advantages are accomplished and the shortcomings of the prior art are overcome by the improved combination quick disconnect coupling and liquid cutoff valve which comprises two tubular members each having a fluid passage therethrough. The first tubular member is connected to a length of flexible tubing. The second tubular member is connected to a pair of lengths of flexible tubing and has a cylindrical sheath telescopicly circumscribing one end and extending from the second tubular member. The cylindrical sheath is of the proper size and shape for telescopic insertion into the first tubular member and in addition is slidably disposed on the second tubular member. A variety of coupling mechanisms such as lugs or screw threads may be used to retain the first and second tubular members together. A key feature of the invention is the concentric positioning of a third tubular member within the second tubular member. The third tubular member is separately connected to one of the lengths of flexible tubing at one end and has a penetrable, resilient, resealable diaphragm at the other, interior end. A piercing pin is inwardly disposed within and attached on the movable cylindrical sheath and faces the third tubular member. Thus, the piercing pin is adapted for penetrating the diaphragm member when the cylindrical sheet is moved rearwardly on the second tubular member. Therefore, when the piercing pin is exterior to the diaphragm, a first liquid passes through one of the lengths of flexible tubing, into the second tubular member, through the piercing pin, through the first tubular member and out the corresponding length of flexible tubing. However, when the piercing pin is inserted through the penetrable diaphragm, then a second liquid flows through a second length of flexible tubing, through the third tubular member, into and through the piercing pin, the first tubular member and out the outgoing length of flexible tubing. Thus, selective passage of the first or second liquid may be accomplished. In the case of peritoneal dialysis, spent dialysate may be drained from the patient through the second tubular member and when completed, fresh dialysate reintroduced into the patient through the third tubular member.

An additional feature of the first tubular member is the inclusion of a movable sleeve disposed therein and partially closed at one end which serves as a cutoff of liquid flow through the device. A plurality of lugs extend through the movable sleeve and the second tubular member either from the second tubular member towards the sleeve or vice versa. The lugs are positioned so as to engage in corresponding slots integrally formed in either the movable sleeve or the second tubular member whereby the movable sleeve may be advanced either through rotation or by sliding to an open position upon coupling of the first and second tubular members, thereby opening the fluid passage therethrough. Thus, when the first and second tubular members are disconnected the passageway into the patient is sealed. In a preferred embodiment, the movable sleeve comprises a rotatable sleeve which allows the passage of liquid upon rotation to an open position.

As an additional feature, the second tubular member may contain a disc valve rotatably contained therein, constructed and arranged for abutting against, sealing and engagement with the first end of the movable sleeve within the first tubular member. The disc valve is effective in selectively opening a fluid passage through the piercing pin after engagement with the movable sleeve when the movable sleeve is rotated to an open position. Conversely, until such rotation of the disc valve, the piercing pin remains sealed because the disc valve is in a closed position. In addition, the abutment of the disc valve in the first end of the movable sleeve substantially reduces the area contaminated by contact to outside air, thereby reducing microbial contamination of the first and second liquids.

As an additional or alternative means of decontaminating the aforementioned device, a sealable channel through both the first and second tubular members may be incorporated therein. Through the use of a capilary action, and antimicrobial agent such as Betadine ® povidone iodine may be dispensed through the fluid passage so as to substantially sterilize the interior of the device. Upon completion of such sterilization, the antimicrobial agent may be flushed from the system by the passage of spent dialysate or may be drained from the device as required.

An additional feature of the invention is the construction of a tubular cowling concentrically disposed about and attached to the movable cylindrical sheath. The cowling is of the proper size and shape to telescopic reception of and attachment to the first tubular member and may include lugs and threading for attachment thereto. The cowling is designed to prevent the inadvertent digital contamination or finger contact with the cylindrical sheath or the piercing pin, thereby preventing contamination.

In an alternative embodiment of the invention, the piercing pin is inwardly disposed within and attached to the first tubular member rather than the movable cylindrical sheath. Thus, the movable cylindrical sheath serves as a slide check allowing the first and second tubular members to be retained in a first position with the piercing pin exterior to the diaphragm or telescopically joined further so that the piercing pin is inserted through the flexible diaphragm. As an additional alternative, the piercing pin may be disposed within and attached to the movable sleeve and still used in the same manner.

As an additional alternative embodiment of the invention, the previously mentioned cylindrical sheath may be discarded altogether and the piercing pin attached to the first tubular member. The first and second tubular members are then simply joined together in a first position with the piercing pin exterior to the diaphragm or further joined so that the piercing pin penetrates the diaphragm.

The embodiments shown illustrate a movable sleeve which is operable through rotation, an additional alternative embodiment may comprise a slidable sleeve which allows the passage of liquid therethrough upon advancement of the slidable sleeve to an open position.

The coupling mechanism previously described comprises a bayonet lock. A plurality of lugs extend inwardly from the second tubular member and are adapted for locking engagement with the plurality of shoulders or slots disposed about the first tubular member, thereby fixedly positioning the first and second tubular members together in compressing engagement.

As previously mentioned, the movable sleeve includes a partially closed end which preferably includes an aperture therethrough. The aperture is adapted to passage of liquid upon alignment with the corresponding aperture in the first end of the first tubular member.

As an additional feature of the invention, the device may include resilient sealing means disposed between the movable sleeve and the first tubular member in order to ensure liquid tight seal. The resilient sealing means preferably comprises first resilient sealing member disposed between the first end of the movable sleeve and the first end of the first tubular member. The resilient sealing member has an aperture adapted for the selective passage of liquid when aligned with the movable sleeve aperture. The resilient sealing means preferably comprises a plurality of foam pads which may be impregnated with an antimicrobial agent such as betadine to prevent contamination. In all the embodiments described, the coupling devices, both sterilizable and sterility maintaining when the first tubular member and second tubular member are joined in a sterile condition.

As an alternative embodiment, the coupling device may include a resilient sealing means between the first tubular member and the second tubular member in order to insure a liquid tight seal. Again alternatively, the resilient sealing members may comprise elastomeric washers or gaskets shaped to conform to the configuration of the tubular member being sealed.

As an additional feature of the invention, a protective cap member is provided, adapted for engagement with an hermetic sealing of the first tubular member when the first and second tubular members are not joined. The protective cap member comprises a coupling mechanism approximate its distal and adapted for engagement with the previously mentioned coupling mechanism of the first tubular member. As an additional feature, the protective cap may include a resilient antiseptic plug coaxially disposed therein and adapted for telescopic reception by and the sealing of the second end of the first tubular member, thereby decontaminating a substantial portion thereof.

The first tubular member may further include a barbed fitment extending from a first end thereof, constructed and arranged for telescopic insertion into and engagement with the previously mentioned length of flexible tubing.

DETAILED DESCRIPTION OF THE PREFERRED EMBODIMENT

While this invention is susceptible of embodiment in many different forms, there is shown in the drawings and will herein be described in detail, several specific embodiments, with the understanding that the present disclosure is to be considered as exemplification of the principles of the invention and is not intended to limit the invention to the embodiments illustrated.

Figure 11:
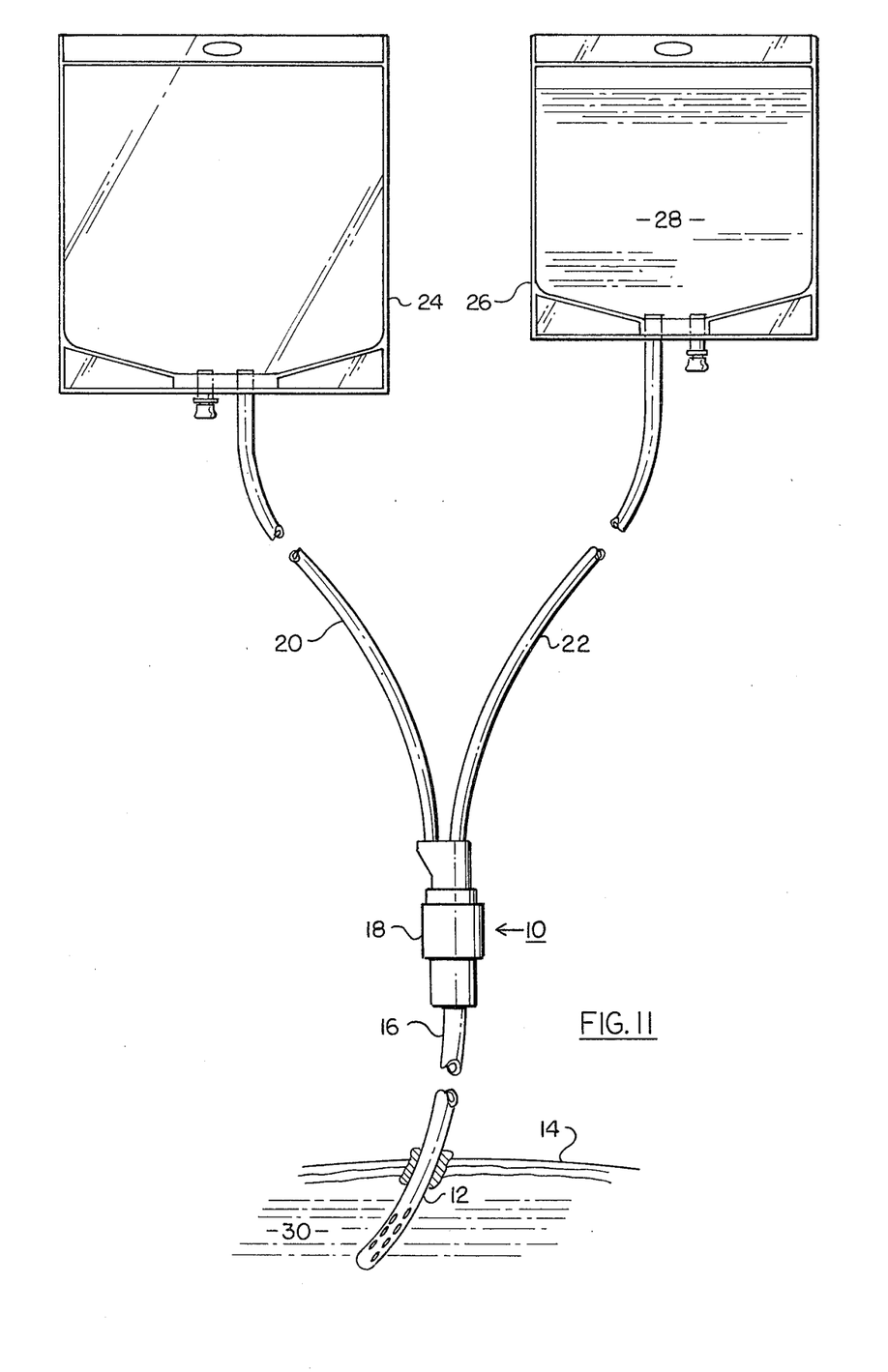
FIG. 11 of the drawings is a front view of a continuous ambulatory peritoneal dialysis system utilizing the improved connector device of the present invention.

As best shown in FIG. 11 of the drawings, continuous ambulatory peritoneal dialysis system 10 comprises a catheter 12 inserted into the peritoneum 14 of the patient 14 and having a length of flexible tubing 16 extending therefrom. At the end of flexible tubing 16 is quick disconnect coupling and fluid cutoff valve 18. Extending from coupling 18 are lengths of flexible tubing 20 and 22. At the end of flexible tubing 20 is empty dialysis bag 24. Similarly, at the end of flexible tubing 22 is filled dialysis bag 26, containing dialysate solution 28. In operation, dialysate solution is initially introduced through quick disconnect coupling 18, flexible tubing 16 and catheter 12 into the peritoneum of patient 14. After a suitable period, usually about four hours, the dialysate solution has absorbed waste products from patient 14 by osmosis through the peritoneum area. At that time, dialysis bags 24 and 26 are connected to quick disconnect coupling 18. Spent dialysate solution 30 is then drained from the patient into empty dialysis bag 24. Thereafter, fresh dialysate solution 28 is administered to the patient through the same quick disconnect coupling fluid cutoff valve 18 and hence through flexible tubing 16 and catheter 12.

Figure 1:
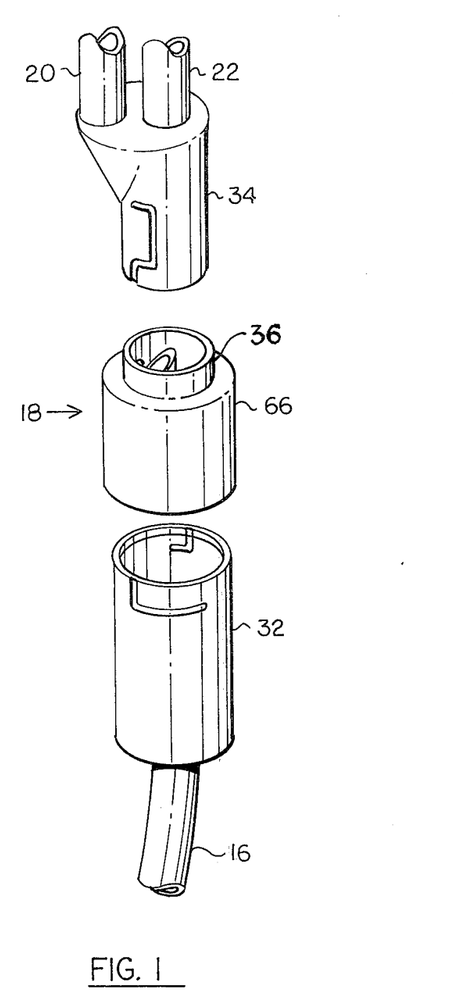
FIG. 1 of the drawings is a front perspective exploded view of an improved combination quick disconnect coupling and liquid cutoff valve.
Figure 2:
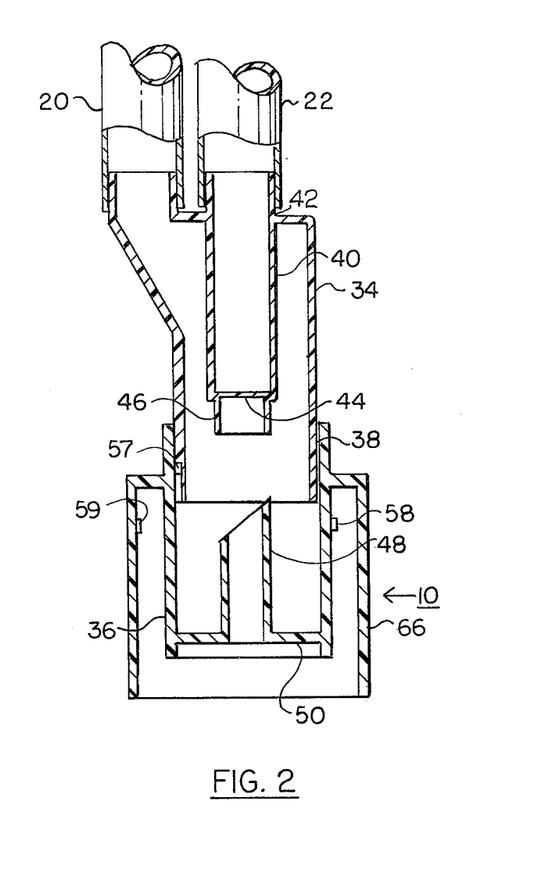
FIG. 2 of the drawings is a vertical section of one portion of the improved combination quick disconnect coupling and liquid cutoff valve of FIG. 1.
Figure 6:
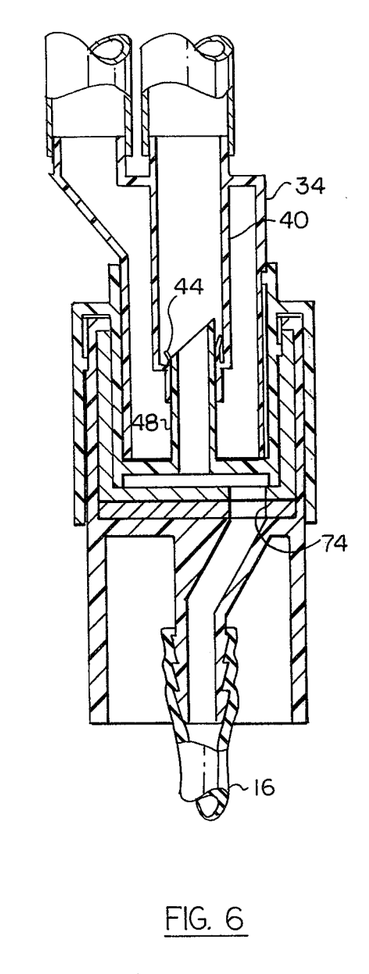
FIG. 6 of the drawings is a vertical section of the quick disconnect coupling of FIG. 1 showing in particular a piercing pin inserted through a penetrate diaphragm resiliently sealing a third tubular member contained within the second tubular member.

As best seen in FIGS. 1, 2, 3 and 3a of the drawings, combination quick disconnect coupling and fluid cutoff valve 18 comprises a first tubular member 32 connected to a length of flexible tubing 16 and being constructed so as to allow the passage of fluid therethrough. Second tubular member 34 is connected to flexible tubing 20 and 22. As shown in FIG. 2, cylindrical sheath 36 telescopically circumscribes portion 38 of second tubular member 34 and extends therefrom. Cylindrical sheath 36 is a tube of a slightly smaller outside diameter than the interior of first tubular member 32 so as to be telescopically insertable therein. In addition, cylindrical sheath 36 is slidably positioned on second tubular member 34, for the following reason. Concentrically positioned within second tubular member 34 is third tubular member 40 which is connected at first end 42 to flexible tubing 22 and is sealed by penetrable, resilient diaphragm member 44 at second end 46. Hollow tubular piercing pin 48 is disposed rearwardly within and is attached to cylindrical sheath 36. In the embodiment illustrated, piercing pin 48 is affixed to sheath 36 by circular collar 50. Thus, spent dialysate solution 30 may pass through first tubular member 32, piercing pin 48, second tubular member 34, flexible tubing 20 and into empty dialysate bag 24 when cylindrical sheath 36 is disposed as shown. When the peritoneum of patient 14 has been emptied, cylindrical sheath 36 may be moved rearwardly on second tubular member 34, so as to cause piercing pin 48 to penetrate resilient diaphragm member 44 (best seen in FIG. 6). As a result, the fluid connection to flexible tubing 20 is sealed, and conversely, the passage of fresh dialysis solution 28 from flexible container 26 through flexible tubing 22, third tubular member 40 and piercing pin 48 may begin. Thus, the selective flow of spent dialysate solution 30 or fresh dialysate solution 28 may be effected simply by operating liquid cutoff valve 18.

Figure 3:
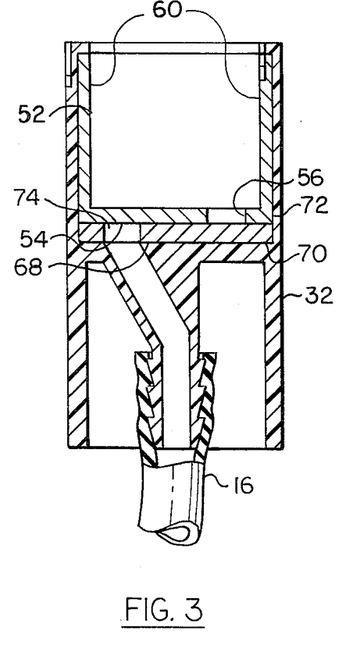
FIG. 3 of the drawings is a vertical section of the improved combined quick disconnect coupling and liquid cutoff valve of FIG. 1 showing a first tubular member adapted for telescopic insertion into and joining with the second tubular member of FIG. 2.
Figure 4:
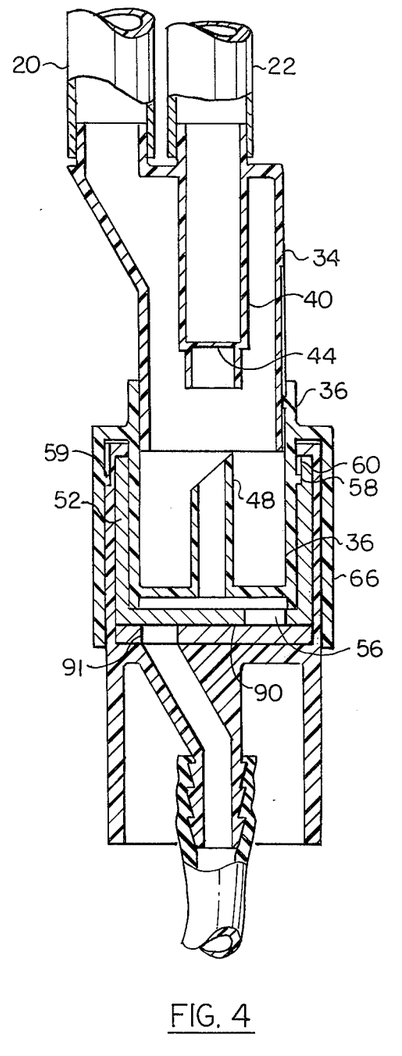
FIG. 4 of the drawings is a vertical section of the improved quick disconnect coupling of FIG. 1 showing in particular a movable sleeve contained within the first tubular member.
Figure 5:
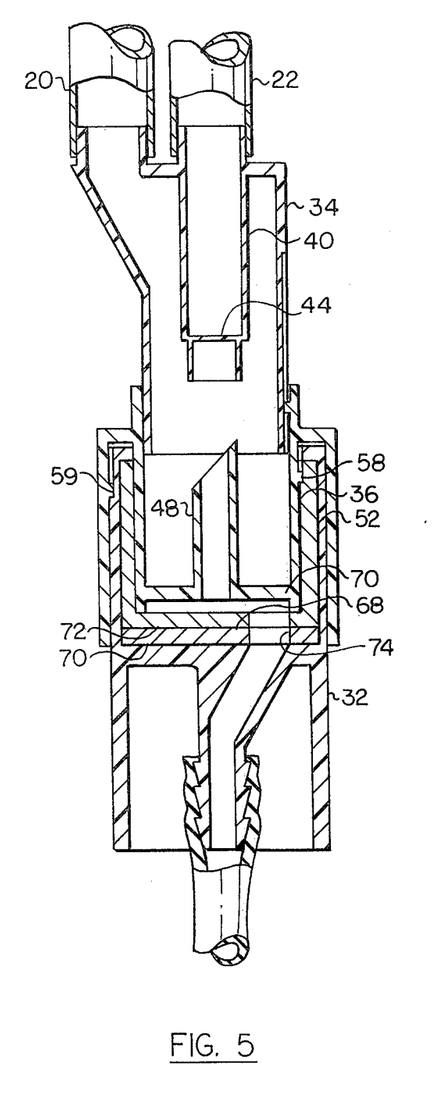
FIG. 5 of the drawings is a vertical section of the improved quick disconnect coupling of FIG. 1 showing in particular rotation of the movable sleeve of FIG. 4 in an open position so as to allow passage of liquid throught the device.

As further seen in FIGS. 3, 4, and 5 of the drawings, in a preferred embodiment, first tubular member 32 includes movable sleeve means 52 disposed within first tubular member 32. Movable sleeve means 52 is partially closed at first end 54 and has aperture 56 extending therethrough. Thus, by moving movable sleeve 52, a passage of fluid through first tubular member 32 may be effected or ceased. In order to effect such movement, lug member 58, shown in FIG. 4, extends between movable sleeve 52 and cylindrical sheath 36. Lug member 58 is constructed and arranged for engagement with corresponding slots 60 integrally formed in movable sleeve means 52 so that as second tubular member 34 is rotated, a corresponding rotation of movable sleeve 52 occurs, thereby opening aperture 56 to the flow of liquid therethrough.

Figure 3A:
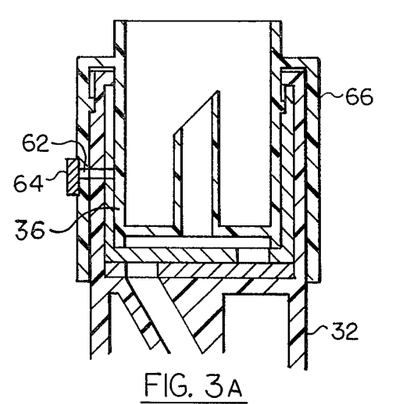
FIG. 3A of the drawings is a vertical section of a portion of the second tubular member of FIG. 2 showing in particular a disc valve and resealable channel into the second tubular member.

As best seen in FIG. 3a of the drawings, in an alternative embodiment, first tubular member 32 and second tubular member 34 may include a resealable channel 62 extending through first tubular member 32, second tubular member 34 and cylindrical sheath 36. In a preferred embodiment, sealable channel 62 includes a disc valve 64 which allows selective passage of liquid therein. Channel 62 includes a series of capillaries extending throughout the device and allowing the passage of an antimicrobial agent such a betadine into the connection so as to substantially sterilize the area therein.

As further seen in FIGS. 1 through 3, second tubular member 34 includes cowling member 66 concentrically disposed about and attached to movable cylindrical sheath 36. Cowling 66 is of an inside diameter slightly larger than the outside diameter of first tubular member 32 so as to telescopically receive first tubular member 32 therein and be attached thereto. Cowling 66 is designed to prevent the digital contamination of cylindrical sheath 36 or piercing pin 48 during connection of the device.

As best seen in FIGS. 3 and 5 of the drawings, first tubular member 32 contains an elastomeric seal 68 within first tubular member 32 at first end 70 of cylindrical recess 72. Elastomeric seal 68 abuts against movable sleeve 52. After cylindrical sheath 36 is inserted into movable sleeve 52 and second tubular member 34 is rotated, aperture 56 is moved into an open position for the passage of liquid through circular aperture 74. Thereafter, rotation of first tubular member 32 causes movable sleeve 51 to rotate until aperture 56 is no longer aligned with aperture 74 so as to prevent the further passage of liquid therethrough. As a result, the flow of liquid between first tubular member 32 and second tubular member 34 may be selectively controlled. In addition, the area exposed to contamination prior to connection is substantially reduced to circular aperture 74, rather than having a flow through a previously contaminated chamber.

As seen in FIG. 4, first tubular member 32 may alternately include a resilient sealing mechanism 90 in the form of a foam pad, rather than an elastomeric seal disposed between movable sleeve 52 and first tubular member 32 so as to hermetically seal same. As shown, resilient sealing member 90 includes aperture 91 which allows the passage of liquid when aperture 56 and movable sleeve 52 is aligned therewith. Resilient sealing member 90 preferably comprises a foam pad impregnated with an antimicrobial agent such as betadine. As a result of this seal, and the presence of an antimicrobial agent, coupling device 18 is both sterilizable and sterility maintaining when first tubular member 32 and second tubular member 34 are joined in a sterile condition. However, in order to allow such sterilization, the material of which connecting mechanism 18 is constructed must be sterilizable, such as polypropylene, polycarbonate or other rigid or semi-rigid plastic materials.

In another embodiment, first tubular member 32 may simply contain piercing pin 48 extending inwardly therefrom and adapted for penetration of pentrable sealing member 44 upon full insertion of second tubular member 34 into first tubular member 32. Again, piercing pin 48 allows the passage of spent dialysate solution 30 until third tubular member 40 is sufficiently advanced so as to cause diaphragm 44 to be pierced by piercing pin 48. Thereupon, fresh dialysate solution 28 flows through piercing pin 48. Similarly, piercing pin 48 may be attached directly to movable sleeve 52 in alignment with aperture 56. Again, the operation of the device is substantially the same. In both of these embodiments, cylindrical sheath 36 is eliminated so that the second tubular member 34 is simply advanced progressively into first tubular member 32, in order to drain spent dialysate solution 30 and then re-infuse fresh dialysate solution 28.

Figure 10:
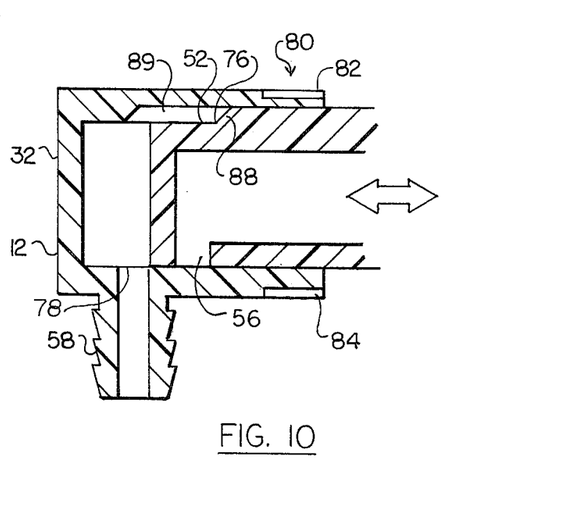
FIG. 10 of the drawings is a vertical section of an additional alternative embodiment of the first tubular member of FIG. 1.

As best seen in FIG. 10 of the drawings, in an alternative embodiment, movable sleeve member 52 may comprise a slidable sleeve member 76 rather than being rotatable as in the previous embodiments. In this case, aperture 56 is aligned with corresponding aperture 78 in first tubular member 32 when flow of liquid is required. As further seen in FIG. 10, the invention further contemplates the use of a coupling mechanism 80 between first tubular member 32 and second tubular member 34 (shown in FIG. 2). In a preferred embodiment, coupling mechanism 80 comprises a bayonet locking mechanism consisting of slots 82 and 84 extending inwardly on first tubular member 32 and adapted for locking engagement with corresponding lugs 58 and 59 (best seen in FIG. 2), disposed within second tubular member 34 so as to fixedly position first tubular member 32 and second tubular member 34 together.

Figure 9:
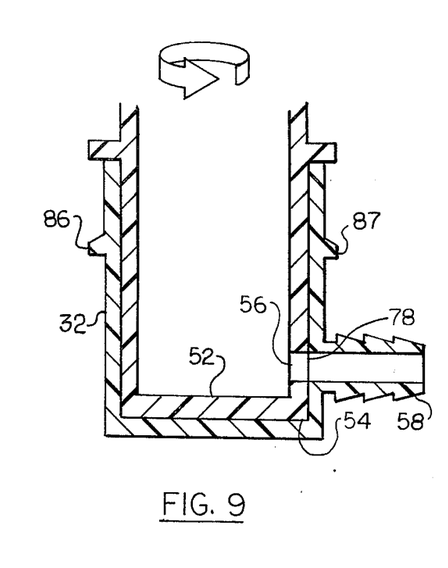
FIG. 9 of the drawings is a vertical section of an alternative embodiment of the first tubular member of FIG. 1.

Alternatively, as seen in FIG. 9, lugs 86 and 87 may extend outwardly on first tubular member 32, adapted for engagement with corresponding slots, (not shown), in second tubular member 34. FIG. 10 further shows that sleeve 76 may be both rotatable and slidable if so desired. In the slidable embodiment, lug 88 is slidably positioned within slot 89 to prevent undesired rotation.

Figure 7:
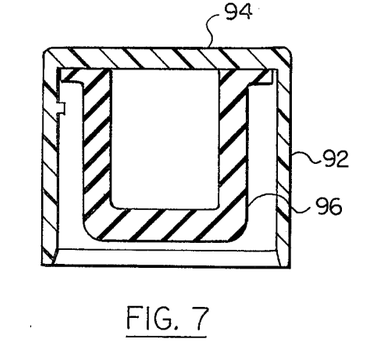
FIG. 7 of the drawings is a protective overcap used to hermetically seal the first tubular member of FIG. 1 when not connected to the second tubular member of FIG. 1.
Figure 8:
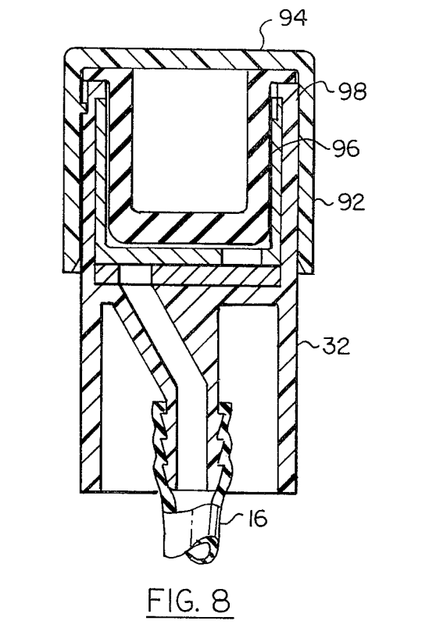
FIG. 8 of the drawings is a vertical section of the first tubular member of FIG. 1 with the protective overcap of FIG. 7 attached thereto.

As best seen in FIGS. 7 and 8 of the drawings, as an additional feature of the invention, protective cap member 92 is provided for hermetic engagement with and hermetic sealing of first tubular member 32. Protective cap 92 comprises a tubular member closed at first end 94 and having an inside diameter slightly larger than the outside diameter of first tubular member 32. As a result, protective cap 94 may be affixed about and hermetically seal first tubular member 32. In addition, protective cap member 92 includes a resilient antiseptic plug 96 coaxially disposed therein and adapted for telescopic reception by and sealing of second end 98 of first tubular member 32.

The foregoing description and drawings merely explain and illustrate the invention, and the invention is not limited thereto, except insofar as the appended claims are limited by those skilled in the art who have the disclosure before them and are able to make modifications and variations therein without departing from the scope of the invention.

I claim:

1. A combination quick disconnect coupling and liquid cutoff valve comprising:

a first tubular member connected to at least one length of flexible tubing and having a fluid passageway therethrough;

a second tubular member connected to a plurality of lengths of flexible tubing and having a cylindrical sheath telescopically circumscribing a portion thereof and extending therefrom constructed and arranged for telescopic connection with respect to said first tubular member; said sheath being movably disposed with respect to said second tubular member;

a third tubular member concentrically positioned within said second tubular member and having a penetrable resilient diaphragm member at a first end and a fluid connection to one of said lengths of said flexible tubing at a second end; and piercing pin means inwardly disposed within and attached to said movable cylindrical sheath and adapted for penetration of said penetrable diaphragm member, said piercing pin means being constructed and arranged for the passage of a first liquid therethrough when said piercing pin means is spaced from said diaphragm member and the passage of a second liquid therethrough when said piercing pin means has been inserted through said penetrable resilient diaphragm member, thereby effecting selective flow of said first or said second liquid as required.

2. The device as disclosed in claim 1 wherein said first tubular member further includes:
  movable sleeve means disposed within said first tubular member, partially closed at a first end, for the selective opening or closing of said fluid passageway;
  a plurality of lug members extending between said movable sleeve means and said cylindrical sheath, constructed and arranged for engagement with a plurality of corresponding slots integrally formed in said sleeve means or, alternatively, said cylindrical sheath, said lug members being effective to advance said movable sleeve member to an open position upon coupling of said first and second tubular members, thereby opening said fluid passageway.

3. The coupling device as disclosed in claim 2 wherein said movable sleeve means comprises a rotatable sleeve member constructed and arranged for the passage of liquid therethrough upon the rotation of said rotatable sleeve member to an open position.

4. The device as disclosed in claim 2 wherein said second tubular member further includes;
  disc valve means rotatably contained therein, said disc valve means being constructed and arranged for abutment against said sealing and engagement with said first end of said movable sleeve means, said disc valve means being effective to selectively open a fluid passage through said piercing pin means upn movement of said movable sleeve means to an open position, and to seal said piercing pin means when said disc valve is in a closed position, said abutment of said disc valve and said first end of said movable sleeve being further effective to substantially reduce the area of microbial contamination to which said liquids are exposed.

5. The device as disclosed in claim 1 and further including sealable channel means into said coupling members for the selective passage of a liquid antimicrobial agent throughout the fluid passage therein.

6. The device as disclosed in claim 1 and further comprising a cowling member concentrically disposed about and attached to said movable cylindrical sheath member, said cowling member being constructed and arranged for the telescopic reception of and attachment to said first tubular member, said cowling member further being adapted to prevent the inadvertent digital contamination of said cylindrical sheath member or said piercing pin means.

7. A combination quick disconnect coupling and liquid cutoff valve comprising:
  a first tubular member connected to a plurality of lengths of flexible tubing and having a plurality of fluid passageways therethrough;
  a second tubular member connected to a plurality of lengths of flexible tubing and having a cylindrical sheath extending therefrom constructed and arranged for telescopic insertion into first tubular member; said sheath being movably disposed on said second tubular member;
  coupling means for the selective engagement and retention of said first tubular member to said second tubular member;
  a third tubular member concentrically positioned within said second tubular member and having a penetrable resilient diaphragm member at a first end and a fluid connection to one of said lengths of said flexible tubing at a second end; and
  piercing pin means inwardly disposed within and attached to said first tubular member and adapted for penetration of said penetrable diaphragm member, said piercing pin means being constructed and arranged for the passage of a first liquid therethrough when said piercing pin means is exterior to said diaphragm member and the passage of a second liquid therethrough when said piercing pin means has been inserted through said penetrable resilient diaphragm member.

8. The device as disclosed in claim 7 in which said piercing pin means is disposed within and attached to said movable sleeve means.

9. A combination quick disconnect coupling and liquid cutoff valve comprising:
  a first tubular member connected to a plurality of lengths of flexible tubing and having a plurality of fluid passageways therethrough;
  a second tubular member connected to a plurality of lengths of flexible tubing constructed and arranged for telescopic insertion into first tubular member;
  coupling means for the selective engagement and retention of said first tubular member to said second tubular member;
  a third tubular member concentrically positioned within said second tubular member and having a penetrable resilient diaphragm member at a first end and a fluid connection to one of said lengths of said flexible tubing at a second end; and
  piercing pins means inwardly disposed within and attached to said first tubular member and adapted for penetration of said penetrable diaphragm member, said piercing pin means being constructed and arranged for the passage of a first liquid therethrough when said piercing pin means is exterior to said diaphragm member and the passage of a second liquid therethrough when said piercing pin means has been inserted through said pentrable resilient diaphragm member.

10. The coupling device as disclosed in claim 2 wherein said movable sleeve means comprises a slidable sleeve member constructed and arranged for the passage of liquid therethrough upon the advancement of said slidable sleeve member to an open position.

11. The connecting device as disclosed in claim 1 further comprising coupling means for the selective engagement and retention of said first tubular member to said second tubular member.

12. The connecting device as disclosed in claim 11 wherein said coupling means comprises a bayonet locking mechanism comprising a plurality of lug members extending outwardly from said first tubular member and adapted for locking engagement with a plurality of slots disposed within said second tubular member, thereby fixedly positioning said first and second tubular members together in compressive engagement.

13. The connecting device according to claim 2 whereas said partially closed end of said movable sleeve means includes an aperture therethrough, adapted for the passage of liquid upon alignment with a corresponding aperture in the first end of said first tubular member.

14. The coupling device as disclosed in claim 2 further comprising resilient sealing means disposed between said movable sleeve means and said tubular member.

15. The coupling device as disclosed in claim 14 wherein said resilient sealing means comprises a first resilient sealing member disposed between said first end of said movable sleeve means and the first end of said first tubular member, said resilient sealing member having an aperture adapted for the selective passage of liquid therethrough.

16. The coupling device as disclosed in claim 14 or 15 wherein said resilient sealing means comprises a plurality of foam pad members impregnated with an antimicrobial agent.

17. The coupling device as disclosed in claim 13 wherein said antimicrobial agent comprises betadine solution.

18. The coupling device as disclosed in claim 1 or 14 wherein said coupling device is sterilizable and sterility maintaining when said first tubular member and said second tubular members are joined in a sterile condition.

19. The coupling device as disclosed in claim 18 further comprising resilient sealing means disposed between said first tubular member and said second tubular member.

20. The coupling device as disclosed in claim 14 wherein said resilient sealing members comprise elastomeric washers or gaskets shaped to conform to the configuration of the tubular member to be sealed.

21. The coupling device as disclosed in claim 1 further including a protective cap member adapted for engagement with and hermetic sealing of said first tubular member when disconnected from said second tubular member, said protective cap member comprising coupling means proximate its distal end and adapted for engagement with said coupling means of said first tubular member.

22. The coupling device as disclosed in claim 21 wherein said protective cap member further comprises a resilient antiseptic plug member coaxially disposed therein and adapted for telescopic reception by and the sealing of the second end of said first tubular member.

23. The coupling device as disclosed in claim 1 wherein said first tubular member includes barbed fitment means extending from the first end of said first tubular member, constructed and arranged for telescopic insertion into and engagement with said length of flexible tubing and for fixed attachment thereto.

* * * * *